United States Patent [19]
Weenig

[11] Patent Number: 5,279,587
[45] Date of Patent: Jan. 18, 1994

[54] SELF-CLEARING EXTENSION SET APPARATUS AND METHODS

[75] Inventor: Clair S. Weenig, 1198 Estates Dr., Lafayette, Calif. 94549-2749

[73] Assignee: Clair S. Weenig, Lafayette, Calif.

[21] Appl. No.: 36,003

[22] Filed: Mar. 23, 1993

Related U.S. Application Data

[63] Continuation of Ser. No. 799,604, Nov. 27, 1991, abandoned.

[51] Int. Cl.$^5$ .............................................. A61M 5/00
[52] U.S. Cl. .................................... 604/247; 604/27
[58] Field of Search ................. 604/27, 28, 30, 82, 604/83, 85, 87, 88, 246-249, 250, 264, 280-284

[56] References Cited

U.S. PATENT DOCUMENTS

| | | | |
|---|---|---|---|
| 3,316,935 | 5/1969 | Kaiser et al. | 604/250 |
| 4,051,867 | 10/1979 | Forberg | 137/555 |
| 4,334,535 | 6/1982 | Wilson et al. | 604/87 |
| 4,354,492 | 10/1982 | McPhee | 128/214 |
| 4,424,056 | 1/1984 | Urquhart et al. | 604/85 |
| 4,511,352 | 4/1985 | Theeuwes et al. | 604/85 |
| 4,585,435 | 4/1986 | Vaillancourt | 604/27 |
| 4,795,429 | 1/1989 | Feldstein | 604/86 |
| 4,874,369 | 10/1989 | Kulle et al. | 604/86 |
| 4,915,688 | 4/1990 | Bischof et al. | 604/83 |
| 4,946,448 | 8/1990 | Richmond | 604/247 |
| 5,002,528 | 4/1991 | Palestrant | 604/246 |

Primary Examiner—C. Fred Rosenbaum
Assistant Examiner—Manuel Mendez
Attorney, Agent, or Firm—Lynn G. Foster

[57] ABSTRACT

A self-clearing extension set comprising a first shunt flow pathway for direct delivery of liquid from a source of pressurized liquid to a patient catheter and a second shunt flow pathway wherein injected fluid is cleared from an add-site to the patient catheter by selectively diverted flow from the source. Two methods and associated apparatus for injecting biologically active liquid and clearing the injected liquid through a smaller lumen of a dual lumen extension tube are disclosed. Two methods for occluding one flow pathway while providing a patent flow pathway through the other flow pathway are also disclosed. Each add-site sealingly accepts a syringe needle which is used to inject biologically active liquid into the second shunt flow pathway. Each add-site comprises a low geometric dead space such that no meaningful quantity of injected liquid remains in the add-site after the rest of the injected bolus of liquid has been cleared to the patient catheter. Novel methods and apparatus for connecting to the dual lumen extension tube, and particularly for connecting to the smaller lumen of the extension tube, are disclosed.

16 Claims, 4 Drawing Sheets

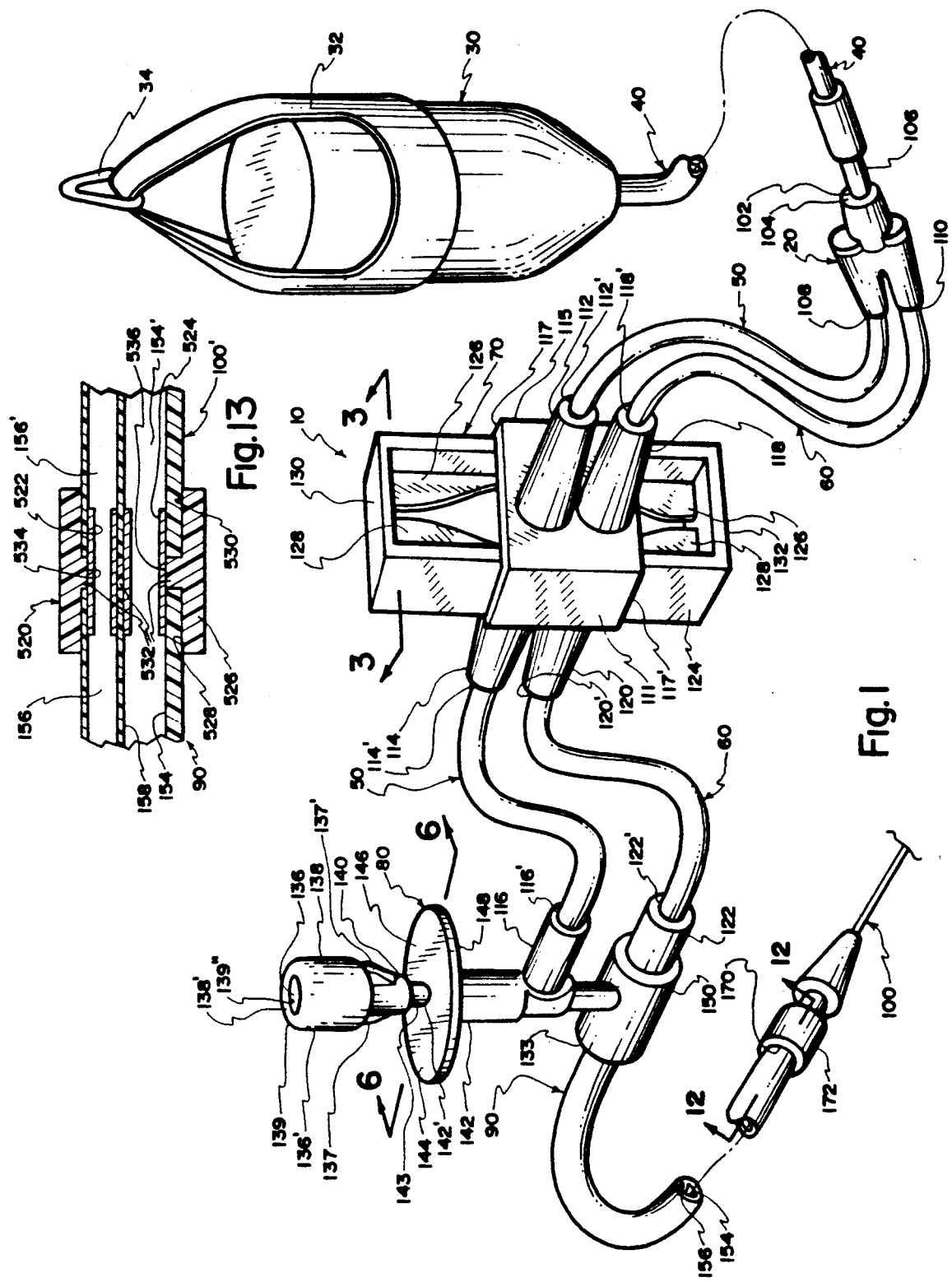

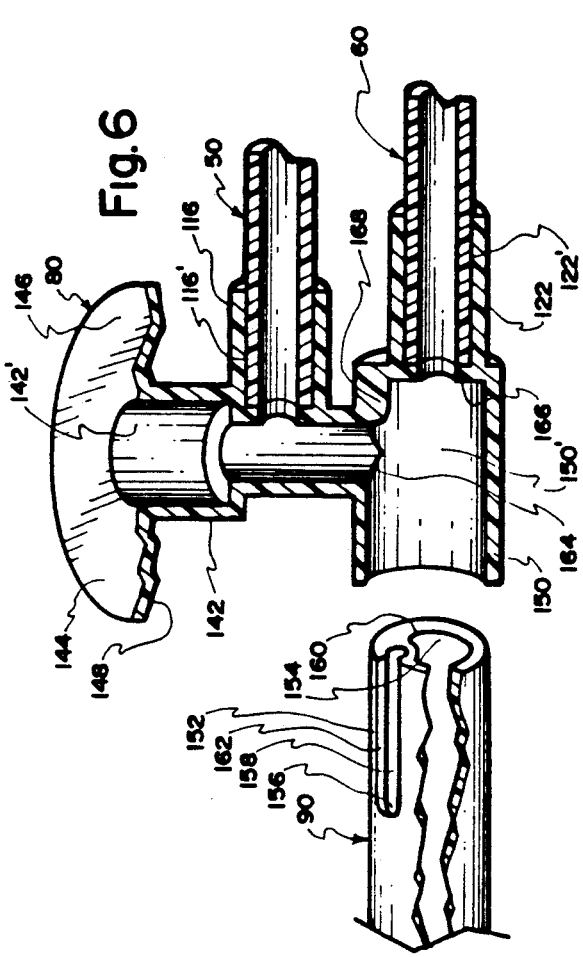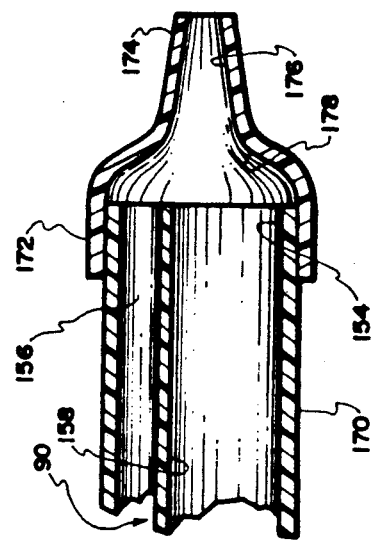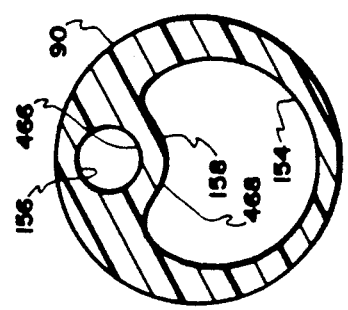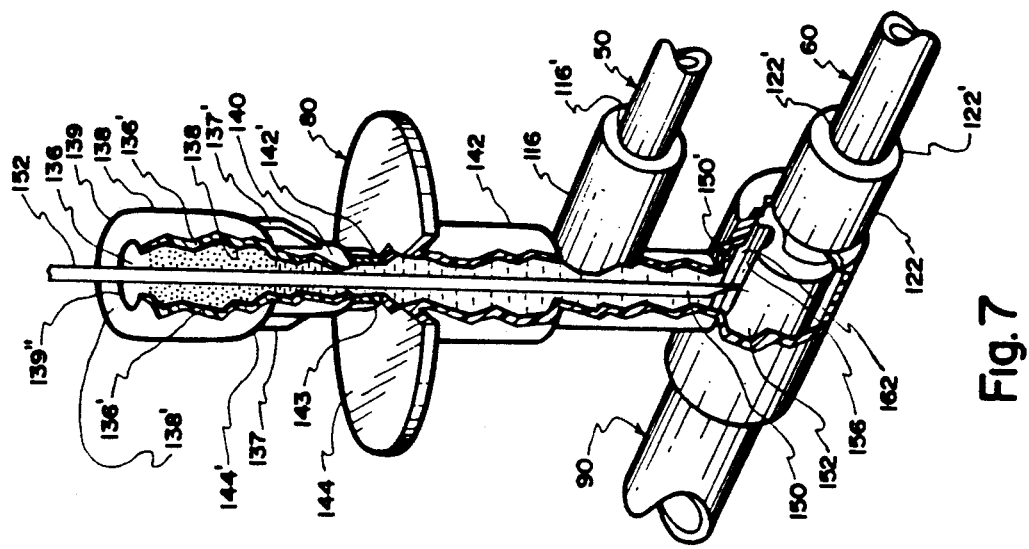

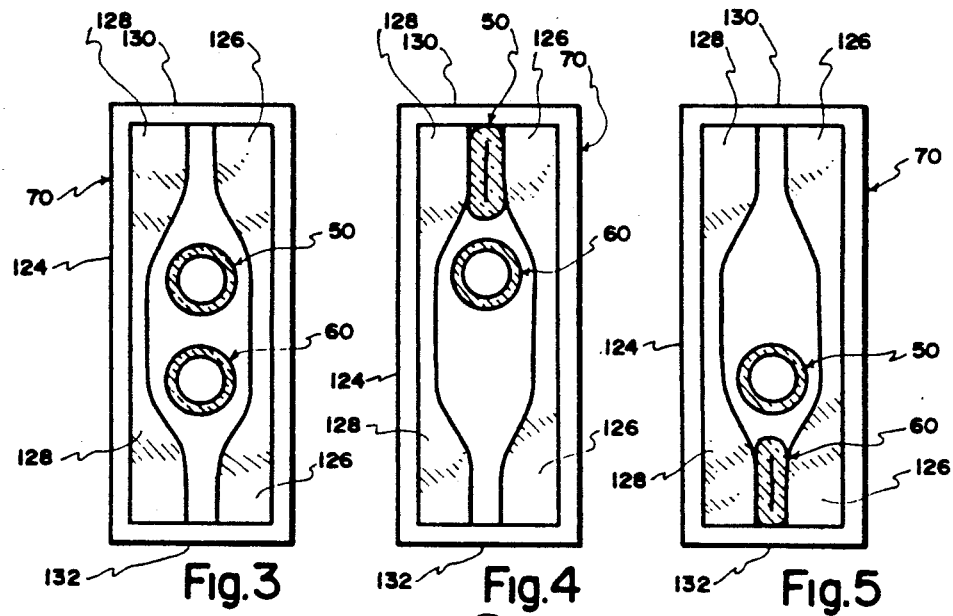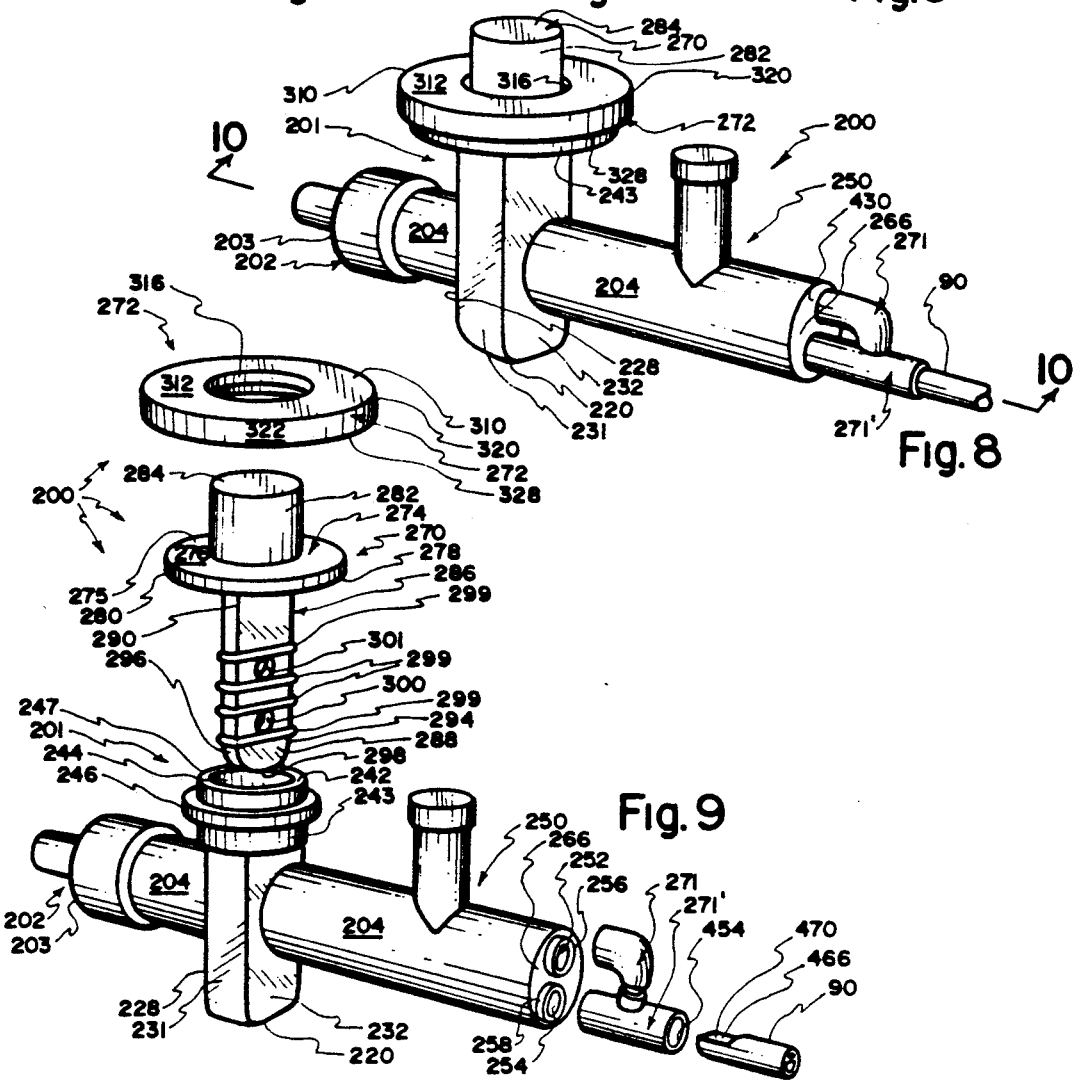

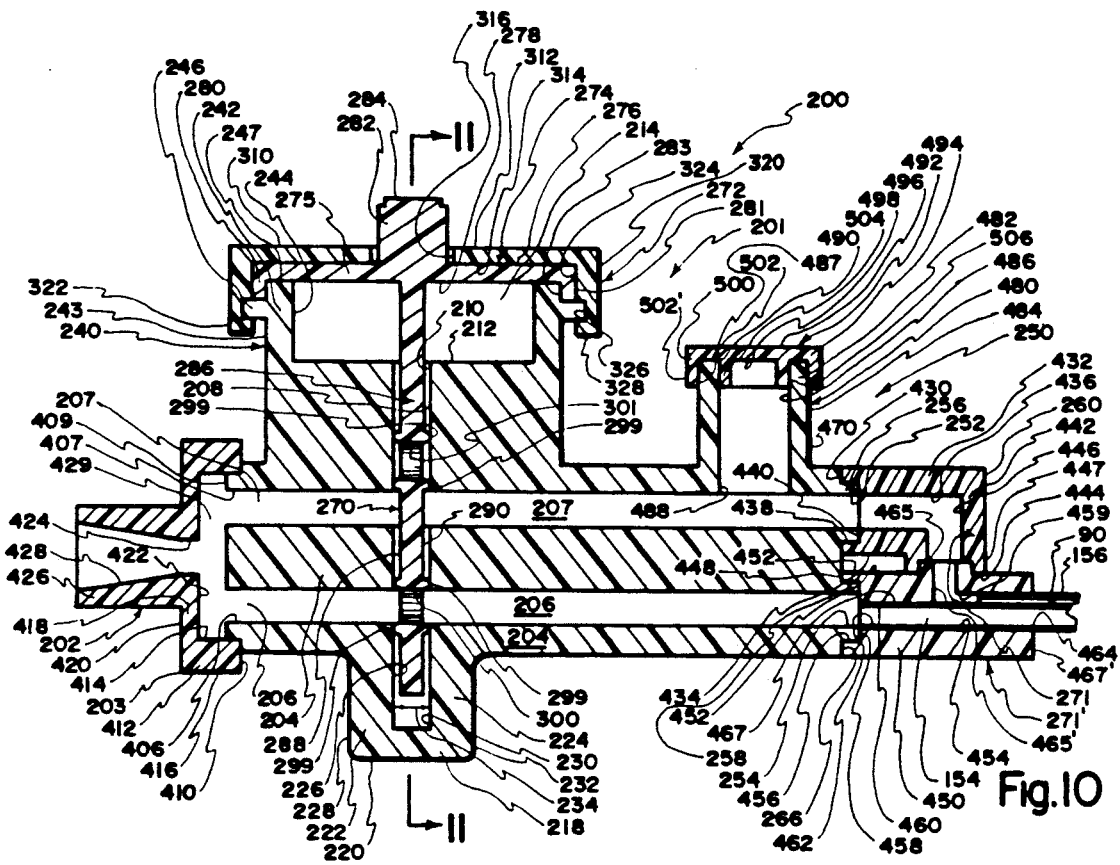
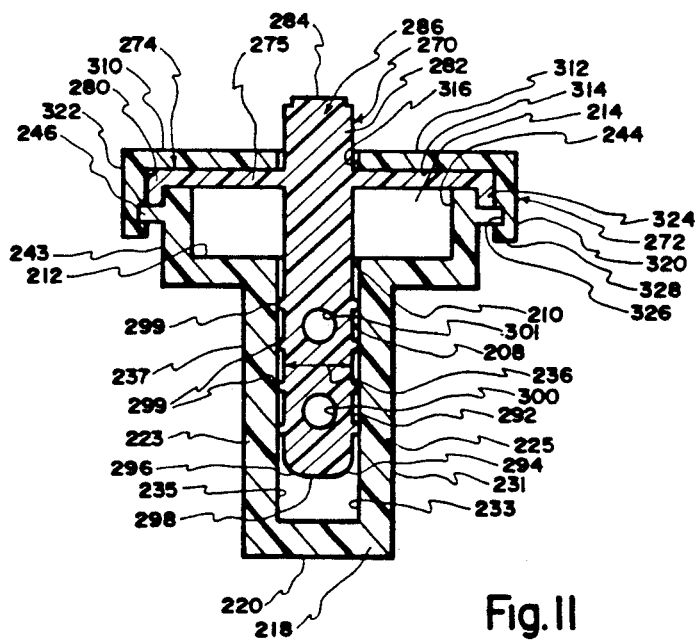
Fig.10
Fig.11

SELF-CLEARING EXTENSION SET APPARATUS AND METHODS

CONTINUITY

This application is a continuation of my co-pending U.S. patent application Ser. No. 07/799,604 filed Nov. 27, 1991, now abandoned.

FIELD OF INVENTION

This invention relates to an extension set for intermittent delivery of biologically active materials during a medical procedure and in particular to a low dead space, self clearing extension set and method for intermittent delivery of biologically active materials during a medical procedure.

BACKGROUND AND DESCRIPTION OF RELATED ART

In modern medical practice, it is common to infuse more than one medicating liquid into a patient at the same or nearly the same time. For this purpose, multi-lumen IV infusion devices are frequently used so that a single patient infusion site may be employed. Most multi-lumen systems are of the type wherein the multiple lumen feature is incorporated within the intravascular catheter itself, and are usually used for more invasive IV approaches as subclavian, internal jugular, or for venous access via a cut down procedure. Some existing multiple lumen IV devices require an entire IV system to be set up for each of the infusion channels being used. The set up includes an IV fluid bag, the IV administration tubing set, and, if extra length is desired, an extension set for each channel as well.

One system, available from Abbott Laboratories, Inc., does allow a two channel infusion into one venipuncture, with the double channel being external to the patient. However, the Abbott system requires a duplicate set of fluid bags, administration sets, and extension tubing.

One method of infusing of a plurality of medications externally into a single lumen catheter is through the use of an extension set. Use of various kinds of extension sets are known in the art. Extension sets are available in the art for continuous and intermittent delivery of medications through an IV tube to an indwelling patient catheter. For such purposes, "Y" connections are provided at an upstream site in the extension set where injection is made. Often a hypodermic syringe is used to pierce a self-sealing diaphragm at the end of one branch of the "Y" connection to introduce a medication into a single orifice extending tube of the extension set.

A significant problem of introducing such medications at an upstream site to flow therefrom to an indwellng infusion catheter through such a single orifice tube is mixing which occurs with other fluids resident in the tube and a resultant dilution of the medicant which occurs prior to reaching the indwelling patient catheter. Such mixing and dilution changes the time course and concentration of the administered drug and the ensuing patient response.

Some IV infused drugs are powerful in very small amounts, such as Nitroglycerine, Nitroprusside, Xylocaine, Dopamine, and Isuprel. During administration of such drugs, it often becomes necessary to rapidly slow down or quickly halt the drug infusion rate due to an exaggerated response of the patient. In IV tubing systems where there is any upstream mixing, all infusion must be stopped entirely to quickly halt the drug infusion. A common complication of stopping all IV flow is clotting which can result in a lost IV infusion site. Recovery of the IV infusion site raises the risk that a new IV bottle and administration set may be used, but the same extension set may be retained whereupon the new IV fluid is "flushed in" through the extension set containing a portion of the drug previously stopped. The previously stopped drug is then flushed through to cause an undesired patient response.

An example of a drug administered by IV which requires a precise titration to a patient is IV Dopamine, a commonly given IV medication for hypotension. The administration of Dopamine is often complicated by a need to rapidly infuse a large volume of fluid concurrent with the Dopamine infusion to augment blood pressure.

The above cited examples of problems associated with very potent medications demonstrate the need for carefully controlling administration rates and delivering some medications separately from other IV infused liquids. For these purposes and to provide a haltable medication delivery pathway, a dual lumen extension set having one smaller lumen and one larger lumen is used. Such medication is normally delivered through the smaller lumen while the larger lumen is used to maintain a second, and perhaps greater, liquid infusion rate.

One of the major problems associated with infusion of drugs into extension sets upstream from an indwelling catheter is dead space. Dead space may be considered to be of two types, geometric and dynamic. Geometric dead space is defined as the space within a device which is not functionally useful, such as a portion of the space within a device which receives a bolus of liquid but from which the share of liquid received by the dead space does not evacuate immediately when the rest of the liquid is washed therefrom. Most often liquid captured in a geometric dead space washes out over a relatively long period of time thereby diluting and distorting the downstream effect of the liquid medication injected as a single bolus into the device. Dynamic dead space is defined as space which is completely cleared by a single wash, but only after a primary injecting function is completed and a subsequent clearing wash function is later performed. Any delay in performing the clearing function also distorts the downstream effect of an injected bolus of medication.

Clinicians frequently increase a cleansing flow of saline or other high volume wash fluid through a known geometric dead space containing device to a "wide open" state for a brief period to wash out the liquid retained in the geometric dead space. Such a "wide open" state of flow into any indwelling catheter is potentially hazardous if left open for too long a time. Bedside processes involved in correcting for inherent geometric dead space are therefore both detrimental to efficiently providing patient IV care and, in some circumstances, life threatening.

A proposed solution to the problems of geometric dead space and dilution of an administered medication through an extension set is advanced in U.S. Pat. No. 4,585,435 which discloses a dual lumen extension tube and a "Y" connection wherein a bolus of medication is delivered by a syringe needle inserted through a sealable membrane into one lumen of the extension tube which is described as being substantially smaller than the other lumen. Flow from both lumens is delivered to a common distal site near the influent port of the patient catheter.

While the medication is sent through the smaller lumen of the extension tube toward the influent port of the patient catheter in a substantially undiluted state, a significant portion of the injected liquid medication remains upstream in the smaller lumen at the end of the syringe needle injection. In order for the total bolus of medication to be delivered to the indwelling patient catheter, an injection of wash liquid must be delivered by a second injection procedure. This second procedure may be time consuming and involve an undesirably delay.

As a result, delivery of the total medication is provided in two discreet time periods. A first partial bolus of the medication is delivered to the patient substantially simultaneously with the syringe injection. Later, a second remaining bolus of medication is delivered at a time dependent upon the speed and dexterity of the technician in removing the syringe and injecting a wash solution with a second syringe. Thus, even though a very small geometric dead space is inherent in the smaller lumen, the delay in washing out the second remaining bolus appears as a dynamic dead space in the delivery of the total medication to the patient.

BRIEF SUMMARY AND OBJECTS OF THE INVENTION

In brief summary, this novel invention alleviates all of the known problems related to efficiently delivering an injected bolus of biologically active liquid through an extension set. This invention provides a self-clearing apparatus whereby only one manual injection procedure is required. The apparatus comprises a dual lumen extension tube, an anaerobic, self-sealing add-site and a fluid gate disposed upstream from the add-site which selectively switches the flow of pressurized liquid flowing from a source to the add-site. The fluid gate also selectively diverts flow to another infusion flow pathway.

Under control of the fluid gate disposed in one state, liquid is steered from the source directly to the patient catheter through a larger lumen of the dual lumen extension tube. Also under control of the fluid gate in a second state, liquid from the source is serially communicated with the add-site. The add-site comprises a very small geometric dead space such that no physiologically meaningful amount of the injected liquid is retained upstream from patient catheter following an infusion cycle. Downstream, flow from the add-site communicates with the smaller lumen of the dual lumen extension tube. The flow path of the smaller lumen is joined with the flow path of the larger lumen at a downstream connector which joins the dual lumen extension tube to the patient catheter.

At the beginning of an injection cycle, the fluid gate is normally steering flow from the source through the larger lumen. A syringe needle is inserted into the add-site and a bolus of biologically active liquid is injected therein. By switching the fluid gate to divert flow from the source to the second infusion flow path immediately after injection of the bolus of biologically active liquid, the add-site and smaller lumen of the extension tube is essentially completely cleared and the medication is rapidly communicated in an essentially undiluted state to the indwelling patient catheter resulting in a physiologically insignificant dynamic dead space. After the add-site and smaller lumen are so cleared, the fluid gate is switched to the prior position to again steer flow through the larger lumen.

Within the scope of the invention, the fluid gate comprises a double throw fluid gate or a normally closed two position fluid gate. In the case of the double throw fluid gate, the fluid gate is manually switched to the infusion state at the beginning of an infusion cycle and thereafter manually returned to a non-infusion position to divert source liquid into the larger lumen of the completion the of infusion cycle. The double throw fluid gate also comprises an intermediate state wherein flow is permitted through both channels at the same time. Thereby, the gate is operably positioned to permit flow in both flow paths at the same time. Thus, the gate is set into the intermediate state to deter tubing within the gate from taking a pathway occluding set during long term use, to provide a dual pathway for slow, controlled delivery of medicating fluid from the add-site, and to permit a continuous flow through the add-site during non-injecting periods to keep liquid in the add-site in a fresh state by a constant flow of liquid therethrough.

In the case of the normally closed two position fluid gate, an actuator is selectively held open to clear the add-site and smaller lumen of the extension tube and then released to automatically return source liquid flow to the larger lumen.

Accordingly, it is a primary object to provide a self-clearing multiple lumen extension set for delivery of biologically active liquid to a patient catheter.

It is another primary object to provide a method for delivering biologically active liquids to a patient insertion catheter comprising only one manual liquid injection step.

It is a very important object to provide an extension set comprising an add-site in which the resulting effects of dilution and distortion associated with geometric and dynamic dead space are not medically significant.

It is a principal object to provide an extension set comprising a first flow path and a second flow path for liquid to flow to a patient catheter from a pressurized source comprising a fluid gate for alternately occluding one flow path and for opening the other flow path therefrom.

It is another object to provide a fluid gate having two flow path occluding positions and a third intermediate position whereat both flow paths are open, the third intermediate position being used for deterring tubing within the gate from taking a set during long term use of the invention, for providing a dual pathway for slow, controlled delivery of fluid from the add-site, and for permitting continuous flow through the add-site during non-injecting periods to keep liquid in the add-site in a fresh state by a constant flow of liquid therethrough.

It is another object to provide a gate having a two position, single channel fluid gate wherein one of the positions is normally closed relative to one of the two flow paths.

It is another object to provide a fluid gate which comprises a slider valve.

It is another object to provide a slider in the slider valve which automatically returns to a first position after being released from actuation at a second position.

It is a main object that the extension set provide a dual lumen extension tube having a larger lumen for direct delivery of pressurized liquid from a source and a smaller lumen wherethrough the injected biologically active liquid is rapidly delivered by flow of fluid from the source.

It is another main object to provide an add-site which sealingly receives a hypodermic needle through which biologically active liquid is transmitted.

It is another main object to provide an add-site whereby biologically active liquid is anaerobically added to a clearable flow path.

It is yet another main object to provide an add-site which comprises a sufficiently small geometric dead space such that no meaningful amount of injected biologically active liquid remains at the add-site after an injected bolus liquid is cleared to the patient catheter.

It is another object to provide luer lock connectors on each end of the extension set for facile connection to upstream and downstream connectors.

These and other objects and features of the present invention will be apparent from the detailed description taken with reference to accompanying drawings.

BRIEF DESCRIPTION OF THE DRAWINGS

FIG. 1 is a perspective of a first embodiment of a rapid infusion extension set.

FIG. 2 is a cross section of a dual lumen extension tube used in the extension set which is somewhat magnified for clarity of presentation.

FIG. 3 is a section taken along lines 3—3 in FIG. 1 wherein a superior patent tube and an inferior patent tube are shown in cross section framed by a slidable section of a pinch valve.

FIG. 4 is a section similar to the section seen in FIG. 3 wherein the pinch valve is seen compressively closing the superior tube.

FIG. 5 is a section similar to the section seen in FIG. 3 wherein the pinch valve is seen compressively closing the inferior tube.

FIG. 6 is a perspective section taken along lines 6—6 of FIG. 1, somewhat magnified to show detail with more clarity.

FIG. 7 is a perspective of the part seen in FIG. 6 combined with other parts to complete a liquid injection assembly with a section removed to show a hollow needle inserted therein.

FIG. 8 is a perspective of a second embodiment of a liquid path valving and injection assembly of a rapid infusion extension set.

FIG. 9 is an exploded perspective of the assembly of FIG. 8.

FIG. 10 is a cross-section taken along lines 10—10 of FIG. 8.

FIG. 11 is a cross-section taken along lines 11—11 of FIG. 10.

FIG. 12 is a cross-section of a distal fitting taken along lines 12—12 of FIG. 1.

FIG. 13 is a cross-section of a distal connecting fitting between the dual lumen extension tube and a dual lumen catheter.

DETAILED DESCRIPTION OF THE ILLUSTRATED EMBODIMENTS

In this description, the term proximal is used to indicate the segment of the device normally closest to a pressurized source of liquid with which is being used. The term distal refers to the other end of the device. The adjective patent is used to qualify a hole or lumen as being open or capable of communicating liquid therethrough. The term biologically active liquid refers to any drug and any other liquid injectable into a patient catheter through an extension set during a medical procedure. The term extension set is used to describe a device serially interposed between a pressurized liquid source and a patient catheter and which provides access for delivery of biologically active liquids. Dead space as defined earlier comprises geometric and dynamic dead space. Geometric dead space is space within a device which is not functionally useful, such as a portion of the space within a device which receives a bolus of liquid but from which the share of liquid received by the geometric dead space does not wash out when the rest of the liquid is evacuated from the device. Dynamic dead space is space which retains liquid after an injection into the device by a first injection procedure and delivers the liquid from the device by a second later flush procedure.

Reference is now made to the embodiments illustrated in FIGS. 1-11 wherein like numerals are used to designate like parts throughout. A first embodiment of an extension set 10 is seen in FIG. 1. In seriatim from the proximal end, extension set 10 comprises a flow divider, a first tube 50, a second tube 60, a slider pinch valve 70, an injector/connector 80 and a dual lumen extension tube 90. Flow divider 20 divides pressurized output flow of patient compatible liquids from a source container 30 and is connected thereto by a tube 40. A permanent sealed liquid connection from flow divider 20 provides a liquid flow path to first tube 50 and second tube 60. Each tube 50 and 60 passes through slider pinch valve 70 and therefrom to be sealably connected to injector/connector 80. Injector/connector 80 connects to a dual lumen extension tube 90 which ultimately communicates with a patient catheter 100.

Liquid pressure from source 30 is generally derived by hanging the source 30 a predetermined distance above the introduction site of the patient catheter 100. As seen in FIG. 1, source 30 generally comprises a hanging implement. For this purpose, source 30 is disposed in a hanging cover 32 which is attached to a triangular ring hanger 34 as seen in FIG. 1.

Flow divider 20 is preferably injection molded from substantially rigid synthetic resinous material from which medical device connectors are made. A material such as ABS may be used. Such material is well known and available in the art. In this embodiment, flow divider 20 may comprise a female luer connector 102 on the proximal common entry end 104 whereby a male connector 106 disposed on the distal end of tube 40 is attached by methods well known in the art. As one skilled in the art understands, other types of connectors may be used within the scope of the invention. Each tube 50 and 60 may be made from medical grade tubing which comprises restorative memory and which can be compressively occluded without splitting. Such tubing materials are also well known and available in the art. In assembly, each tube 50 and 60 is permanently bonded otherwise sealably affixed on one end to a distal port 108 and 110, respectively, of flow divider 20.

valve 70 comprises a rectangular guide ill which provides support for two pair of juxtaposed tube guides 112 and 114 and 118 and 120 as seen in FIG. 1. Rectangular guide 111 comprises a vertically disposed rectangular wall 115 and top and bottom blunt ends 117 and 117', respectively. Each tube guide 112, 114, 118, 120 is medially disposed and vertically aligned on a side of wall 115 as seen in FIG. 1. Each tube guide 112, 114, 118, and 120 comprises a through-bore 112', 114', 118', and 120' which is greater in diameter than the external diameter of each of tubes 50 and 60 such that each tube 50 and 60 move with ease inside each guide 1121, 114, 118, and 120 when disposed therein. Valve 70 further comprises an open ended box shaped slider 124 disposed inside wall 115.

With slider 124 medially disposed in rectangular guide 111, tube 50, extending from distal port 108, is inserted through one pair of tube guides 112 and 114 on the proximal and distal sides of valve 70, respectively, and extended therefrom into a an orifice 116' of tube receiving female connection 116 of injector/connector 80 whereat a permanent bond or otherwise sealed permanently affixed connection is made. Adhesive materials and procedures for making all permanent connections to injector/connector 80 are well known and available in the art. Similarly from distal port 110, tube 60 is inserted through the second pair of tube guides 118 and 120 on the proximal and distal sides of valve 70, respectively, and extended therefrom into an orifice 122' of receiving female connection 122 whereat another permanent sealed connection is made.

Open ended box shaped slider 124 slides in the vertically disposed rectangular guide 111. As seen in FIGS. 1, and 3-5, slider 124 comprises two longitudinally and centrally disposed members 126 and 128 which in combination describe a central space which is medially sufficiently large to allow passage of tubes 50 and 60 to freely pass therethrough.

However, at each longitudinal end 130 and 132, members 126 and 128 are arcuately curved medially such that a tube 50 or 60 disposed therebetween is compressively occluded. As seen in FIG. 4, when slider 124 is moved downward relative to guides 112, 114, 118, and 120 until tube 50 is disposed at end 130, tube 50 is totally occluded. Similarly, as seen in FIG. 5, when slider 124 is moved upward relative to guides 112, 114, 118, and 120 until tube 60 is disposed at end 132, tube 60 is totally occluded.

Thus, slider valve 70 comprises a three position fluid gate. A first position, with slider 124 downwardly extended as seen in FIG. 5, occludes only tube 50. A second position wherein slider 124 is centrally disposed relative to guides 112, 114, 118 and 120 as seen in FIG. 3 does not occlude either tube 50 or 60. A third position with slider upwardly extended as seen in FIG. 4 occludes only tube 60. As such, slider valve 124 is normally retained in the centrally disposed state when unused, such as in shipment, so that tubes 50 and 60 do not take a permanent set. Further, orifices 112', 114', 118', and 120' are sized to permit slider valve 70 to move along tubes 50 and 60 to reduce the likelihood that only one area of each tube is pinched as each tube 50 and 60 is compressively occluded, thereby extending the useful life of extension set 10.

Referring again to FIG. 1, the distal end of each tube 50 and 60 comprise a proximal input to a an orifice 116' of female connection 116 and an orifice 122' of female connection 122 of injector/connector 80, as previously described. On the distal side 133, injector/connector 80 is connected to dual lumen extension tube 90 as is described in detail hereafter. Injector connector 80 comprises two components, an add-site injector stem 140 and a body 142. At the top, body 142 comprises a substantially planar disk member 144 which further comprises a top receiving orifice 142' medially disposed therein. Stem 140 comprises an inferior segment 143 which is sized to sealingly fit into the top receiving orifice 142' to join stem 140 to body 142. Above inferior segment 143, stem 140 comprises a conically expanding segment 144' which conically expands to provide a cylindrical vessel 136' for a pierceable, compliant membrane 136 disposed therein. Membrane 136 is sufficiently thick and resilient to anaerobically receive a hollow liquid delivery device, such as needle 152 seen in FIG. 7. Supporting struts 137 and 137' are disposed opposite sides of step 140 to strengthen step 140 against breakage when needle 152 is being inserted or withdrawn.

Cylindrical vessel 136' comprises a surface wall 138, which extends interiorly upward to a topmost corner 139 and turns medially thereat to form a superior hollow aperture 139" for cylindrical vessel 136'. From superior hollow aperture 139", surface wall 138 turns sharply outward to form a superior retaining ring 138' for material stored in cylindrical vessel 136'. Retaining ring 138' is provided to hold membrane 136 in place during extraction of a needle liquid delivery device. Similarly, membrane 136 is held in place during introduction of the needle by the inferiorly disposed conically expanding segment 144' of stem 140. In assembly, stem 140 is permanently bonded to body 142.

As best seen in FIGS. 1 and 6, planar disk 144 comprises an upper surface 146 and a lower gripping surface 148, allowing body 142 to be facilely gripped while needle 152 or other liquid delivery device is anaerobically inserted through membrane 136. Upper surface 146 provides a protective shield against an inserting needle 152 when fingers are supportingly placed below disk 144 against lower gripping surface 148. Body 142 extends downward below disk 144 whereat orifice 142' communicates with female connection 116. Continuing downward, body 142 intersects a laterally disposed cylindrical barrel 150 which communicates with female connection 122.

Barrel 150 comprises an open chamber 150', as seen in FIGS. 6 and 7. Thereby, a continuous linear pathway for orifice 142' is defined from the point of insertion of stem 140 to the open chamber 150' of barrel 150. Also, lateral communication pathways are opened to female connections 116 and 122. As best seen in FIG. 7, an inserted hollow needle extends directly into the open chamber 150' of barrel 150 through membrane 136 and orifice 142'.

Juxtaposed connection 122 on the distal side of barrel 150, a specially tooled end 152 of dual lumen extension tube 90 is inserted in a predetermined and keyed orientation. As seen in cross section in FIG. 2, dual lumen extension tube 90 comprises a relatively large lumen 154, a relatively small lumen 156, and a separating membrane 158. Such dual lumen extension tubes are known and available in the art. As will be described in detail later, the size of small lumen 156 is a determining factor in the speed of presentation of an injected bolus of biologically active liquid to patient catheter 100. For this reason, lumen 156 may be less than 1 millimeter in diameter having a total volume in a 100 centimeter length of less than one milliliter. However, the cross section of lumen 156 is not restricted to one millimeter in diameter, as is apparent to one of ordinary skill in the art.

As best seen in FIG. 6, tooled end 152 comprises a square end cut 160 and a slot 162 which is cut a predetermined distance lengthwise therefrom to open lumen 156 from the top thereof. As seen in FIG. 6, open chamber 150' comprises a length which is laterally disposed about an opening 164 of orifice 142' into chamber 150'. At the proximal end 166 tubing 60 is sealingly received and disposed a predetermined distance proximal of opening 164.

Disposed between opening 164 and proximal end 166 is a rib guide 168 which comprises a guide whereby insertion of extension tube 90 is only permitted when slot 162 is aligned with rib guide 164. Thus, slot 162 is used to provide a top opening access for flow of liquid from orifice 142' into lumen 156 and a keying slot for the necessary alignment of extension tube 90 within chamber 150'. When assembling extension tube 90 into chamber 150' extension tube 90 is rotated until slot 162 is aligned with rib 168 and is then inserted into chamber 150' and bonded or otherwise sealably attached thereto. Extension tube 90 is bonded or otherwise permanently affixed in place by materials and procedures which are known and available in the art.

Referring again to FIG. 1, at the distal end 170 of extension tube 90, a connector 172 is provided for connecting extension tube 90 to patient catheter 100. As seen in FIG. 12, connector 172 is permanently joined to extension tube 90 by bonding as previously described for the other attachment of extension tube 90. Connector 172 comprises a luer fitting 174 and an exit orifice 176 for facile connection to patient catheter 100. Internally, connector 172 comprises a low geometric dead space and unrestricted passageway 178 where liquid from each lumen 154 and 156 flows freely to exit orifice 176.

In use, extension set 10 is purged of air and interconnected between source tube 40 of source container 30 and patient catheter 100. Slider valve 70 is set with slider 124 positioned as seen in FIG. 4 whereat tube 50 is occluded and tube 60 is patent. Liquid is thereby delivered from source container 30 through tube 60 to patient catheter 100.

When a bolus of biologically active liquid is to be delivered to patient catheter 100, a needle 152 is inserted through membrane 136 and a bolus of biologically active liquid is injected into the stream of liquid flowing through tube 50 in the vicinity of orifice 164. Slider 124 is then positioned as seen in FIG. 5, closing tube 60 and opening tube 50. Because of the small cross-section of lumen 156, flow of pressurized liquid from source 30 drives the bolus of injected liquid through the small lumen 156 of extension tube 90 to patient catheter 100. Because the orifice size of lumen 156 is much smaller than the orifice 154, end-to-end transport time of liquid in lumen 156 is much shorter than end-to-end transport time of liquid in orifice 154. Also, the relatively small volume and geometric dead space associated with the insertion site results in only minimal mixing. As a result, the injected bolus of liquid is rapidly delivered in a relatively unmixed state to patient catheter 100.

In addition to the use of the second position of slider valve 70 as seen in FIG. 3 as an unused shipping state, slider valve 70 is also positioned thereat to deter tube 50 from taking a set during long periods of operative use of extension set 10. When slider valve is in the second position, liquid flows through tube 60 at one rate and through tube 50 at a relatively slower rate thereby maintaining fresh liquid in open chamber 150' and small lumen 156. As small lumen 156 has a known orifice size relative to large lumen 154, a medicant injected into open chamber 150' is delivered in a slow and controlled manner through the small lumen 156 to patient catheter 100 providing yet another use for the second position of valve 70.

Another currently preferred embodiment is seen in FIGS. 8-11. This embodiment comprises a valve fitting, seen in FIG. 8 and generally designated 200. While performance is not exactly the same, valve fitting 200 functionally replaces flow divider 20, tubes 50 and 60, slider valve 70 and injector/connector 80 in extension set 10 as seen in FIG. 1.

The valve fitting 200 comprises a valve body 201, a valve member 270, a connecting cap 203, an elbow 271, a connecting "T" 271', and a retainer cap 272. The valve body 201, preferably formed as one piece by injection molding, comprises a first cantilevered end 202 by which a connection is made to the connector 106 from source 30 and tube 40 as seen in FIG. 1. End 202 comprises a connection 203 which is functionally the same as connection 104 of extension set 10. Accordingly, no further description of end 202 of fitting 200 is needed.

As best seen in FIG. 10, valve body 201 comprises a central portion 204, which defines two linear passageways 206 and 207, centrally located and axially directed. (See FIG. 10). Passageway 206 is aligned with and is illustrated as having a diameter substantially the same as the interior diameter of lumen 154 of extension tube 90. Axial passageway 206 is subdivided into two juxtaposed sections by a vertically-directed rectangular slot 208. Passageway 207 is vertically offset from passageway 206 and is illustrated as having a diameter substantially the same as the interior diameter of passageway 206 although the diameter may be closer to the diameter of lumen 156 of extension tube 90. Similar to passageway 206, passageway 207 is likewise subdivided into two juxtaposed sections by rectangular slot 208. Vertically-directed, rectangular slot 208 comprises an opening 210 at top surface 212 of the central portion 204. Surface 212 is essentially circular and forms the bottom of a deflection chamber or compartment 214, as explained hereinafter in greater detail.

The slot 208 is vertically elongated and extends, as illustrated in FIG. 10, downwardly to a location substantially below the end 202 of the valve fitting 200. The rectangular slot 208 has a predetermined uniform thickness 234 (FIG. 10) and a substantially vertical width 236 (FIG. 11). The interior bottom surface of the vertical rectangular slot 208 comprises part of a rectangular horizontally-directed wall 218. Wall 218 terminates in exposed rectangular exterior surface 220 and merges with vertically directed transverse walls 222 and 224 and downwardly tapered side walls 223 and 225, respectively. The wall 222 is defined by an interior surface 226 and an exterior surface 228. Wall 224 is defined by interior surface 230 and exterior surface 232. Wall 223 comprises interior surface 235 and exterior surface 237. Wall 225 comprises interior wall surface 233 and exterior wall surface 231. As illustrated, the walls 218, 222, 224, 223, and 225 are illustrated as being of uniform thickness throughout.

Preferably, the valve body member 201 is injection molded of shape-retaining synthetic resinous material, such as rigid ABS.

The relatively massive central portion 204 comprises an integral upwardly directed annular ring or boss 240. Boss 240 comprises an annular wall 242, illustrated as being of substantially uniform thickness throughout. Wall 242 comprises an annular interior surface 244, forming part of the deflection chamber or compartment 214, and an external surface 243, which is generally cylindrical, but interrupted by a horizontally-directed radial lip 246, illustrated as being generally of rectangular cross-section. Annular wall 242 terminates in a blunt upper edge 247.

The relatively massive central portion 204 also comprises a distal end portion, generally designated 250. End 250 is cantilevered generally toward the patient from the central portion 204 and centrally defines the longer of the two sections of the axial bores 206 and 207. The end 250 terminates in a blunt transversely-directed edge 266. As seen in FIG. 9, blunt edge 266 comprises an orifice 252 for an outlet for bore 207 and an orifice 254 for an outlet for bore 206. Each orifice 252 and 254 is surrounded by a rectangular ring 256 and 258, respectively. Rectangular ring 256 provides a female connection for an elbow 271 as is described in detail hereafter. Rectangular ring 258 similarly provides a female connection for a connecting "T" 271', also described in detail hereinafter.

The valve member 270 functions not only to open and close the passageway 206 of valve fitting 200, but acts as its own return spring. As seen in FIG. 10, when valve member 270 is depressed to fully deflect into compartment 214, passageway 206 is closed and passageway 207 is opened. Valve member 270 is formed of silicone rubber or the like which has characteristics of substantial elasticity, substantial memory and substantial compressibility. Valve member 272 comprises an inverted cup-shaped spring member 274. Spring member 274 comprises a disc-shaped diaphragm top 275 which comprises a top surface 276 and a bottom surface 278. The disc-shaped top 275 is illustrated as being of uniform thickness. Disc-shaped top 275 merges at its perimeter with a downwardly-directed annular flange or lip 280, illustrated as being of uniform thickness throughout and comprising outside and inside wall surfaces 281 and 283. The lip 280 is the structure by which the valve member 270 is held in the assembled position illustrated in FIG. 10. The disc-shaped top 275 specifically functions as a diaphragm return spring.

Integral with the disc-shaped top 275 is a centrally-disposed upwardly-projecting cylindrical actuator 282. Actuator 282 terminates in a blunt exposed upper edge 284 and has enough mass and structural integrity so that it does not deflect from side-to-side when depressed.

Also integral with the disc-shaped top 275 is a downwardly directed generally rectangular flat valve plate 286. Valve plate 286 comprises front and back flat surfaces 288 and 290, an edge 292 which runs through 180 degrees from and to bottom surface 298. The edge 292 comprises rounded corners 294 and 296 adjacent the downwardly-directed apex of bottom surface 298 of the edge 292.

The valve plate 286 also comprises lower aperture 300 of predetermined size and location spanning between the surfaces 288 and 290 and an upper aperture 301 of substantially the same size as aperture 300 and also spanning the surfaces 288 and 290. As illustrated, the aperture 300 is located essentially in line with passageway 206 when diaphragm 275 is unstressed. Note that when diaphragm top 275 is unstressed, aperture 300 is thereby aligned with passageway 206 and passageway 207 is occluded. Thereby, aperture 301 is located to be in line with passageway 301 when diaphragm top 275 is fully depressed into chamber 214. When diaphragm top 275 is fully depressed into chamber 214, aperture 301 is aligned with passageway 207 and passageway 206 is occluded by flat valve plate 286.

The width and thickness of the valve plate 286 are predetermined so as to be just slightly less than the thickness 234 and slightly less than the width 236 of the slot 208. Integrally and circumferentially molded upon valve plate 286, above and below each aperture 300 and 301, are four separate horizontal sealing rings 299. Each sealing ring 299 comprises a raised ridge which provides a pressurized liquid seal around each aperture 300 and 301. As seen in FIG. 10, communication of liquid pressure and flow in passageway 206 is sealed from passageway 207 when diaphragm top 275 is unstressed and passageway 207 is occluded. Similarly, communication of liquid pressure and flow is sealed from passageway 206 when diaphragm top 275 is fully depressed into chamber 214. The vertical length of the valve plate 286 is, in an unstressed state, formed so as to extend only partly along the length of the slot 208 so that the aperture 300 is clearly out of alignment with the bore sections 206 when the valve plate 286 is axially compressed. The dimensional relationship between the valve plate 286, sealing rings 299, and the slot 208 is, therefore, such that a seal is created between the surface 290 of the valve plate 286, the sealing rings 299, and the slot surface 230. Thus, when the valve plate 286 is in the unstressed position illustrated in FIG. 10, pressurized liquids flowing into bore 206 at the end 250 flow through aperture 300 of the valve plate 286 to the distal end of passageway 206. As noted above, when diaphragm top 275 is fully depressed into chamber 214, pressurized liquid flowing into bore 207 at end 250 flows through aperture 301 of the valve plate 286 to the distal end of passageway 207.

The retainer cap 272 is preferably formed of shaped-retaining synthetic resinous material and comprises an upper, horizontally disposed wall 310 of uniform thickness comprising a top surface 312 and bottom surface 314. The wall 310 is interrupted by central aperture 316, the diameter of which is larger than the diameter of the cylindrical actuator 282 so that the actuator 282 may reciprocate up and down loosely through the aperture 316. The horizontal wall 310 merges with an annular downwardly directed flange 320 which is integral with the annular wall 310 and extends radially downwardly and comprises exposed annular surface 322 and interior generally annular surface 324. An annular groove 326 is disposed in wall 320 at surface 324 near the lower edge 328, and sized and located so as to snugly fit over the flange 246 and retain the retainer 272 in a snap-fit assembled position as illustrated in FIG. 10 against inadvertent removal. This retains the wall 280 of the valve member 270 in its assembled condition.

Note that the width of downwardly-directed radial flange 280 is sized and shaped to fit compressively between the space created between the walls 242 and 320 with the deflectable disc-shaped top 275 spanning across the cavity 214. Thus, the downward flange or lip 280 is trapped and held in the assembled position by the retainer cap 272 against inadvertent release.

The length of the cylindrical actuator 282 is preferably selected so that manual depression of the same (against the memory of the silicone rubber material from which the disc-shaped top spring member 275 is made) may continue downwardly until the upper blunt surface 284 is essentially flush with the surface 312 of the retainer 272. This forces the valve plate 286 downwardly into the slot 208 a distance sufficient to bring the aperture 301 of the valve plate 286 into alignment with the two bore segments 207. Thus, pressurized flow into proximal cap 203 (See FIG. 8) is communicated through the two bore sections 207, the aperture 301, and the lumen 156 of the extension tube 90.

At end 202, valve body 201 comprises an influent orifice 406 providing influent liquid entry to passageway 206 and an influent orifice 407 providing influent liquid entry into passageway 207. As seen in FIG. 10, a raised rectangular annulus 409 circumscribes the common area of orifices 406 and 407 and provides a female connection for connecting cap 203. Connecting cap 203 comprises a distal blunt end 410 where cap 203 is butted against valve body 201.

An essentially circular wall 412 extends proximally from blunt end 410 and comprises an inner annular surface 414 and exterior annular surface 416. Wall 412 is orthogonally joined to an inwardly directed wall 418 which comprises an exterior surface 420 and an interior surface 422. At the most interior part of surface 422, an orifice 424 is formed to received influent liquid flow. Orifice 424 is approximately the same diameter as passageways 206 and 207.

Extending proximally about orifice 424 from wall 418 is an annular wall 426 which forms a female luer connector 428 into which connection is made from tube 40. When connected to valve body 201, surfaces 422 and 414 and the proximal end of valve body 201 combine to define a space 429 through which liquid freely flows from orifice 424 to either passageway 206 or 207. Cap 203 is preferably injection molded and made from the same material as valve body 201 is made. The diameter of inner annular surface 414 is sized to frictionally fit annulus 409 for a compressive fit thereon. In assembly, cap 203 is permanently affixed to valve body 201 using materials and methods well known in the art.

On the distal end 266, connection is made to the dual lumen extension tube 90 by way of elbow 271 and connecting "T" 271'. Elbow 271 comprises a proximal blunt end 430 from which an annular wall 432 extends distally. Wall 432 comprises an exterior wall surface 434 and a stepped interior wall surface 436. Stepped interior wall surface 436 extends distally a short distance from blunt end 430 along an inner annular wall surface 438 to an inner stepped surface 440. In combination the size and length of inner annular wall surface 438 and inner stepped surface 440 form a compression fit female connection for rectangular shaped ring 256.

Wall 432 is joined to a normally disposed annular wall 442 to form elbow 271. Wall 442 comprises a blunt end 444 and a stepped inner wall 446 which forms a female connector 447 similar to that found on the proximal end of elbow 271 and is therefore not further described herein.

Connecting "T" 271' comprises a blunt annular proximal end 448 from which an annular wall 450 extends distally. Wall 450 comprises an exterior wall surface 452 and a stepped interior wall surface 454. Stepped interior wall extends distally a short distance from proximal blunt end 448 along an inner annular wall surface 456 to an inner stepped surface 458. In combination the size and length of inner annular wall surface 456 and inner stepped surface 458 form a compression fit female connection for rectangular shaped ring 254.

Extending distally from inner stepped surface 458 wall 450 comprises an asymmetric inner surface 459 comprising a superior proximal surface part 460, inferior proximal surface part 462, and a distal surface part 464. Interposed between part 460 and part 464 is a male "T" connection 465 which is sized to compressively join with female connector 447. An upward opening orifice 465' from "T" connection 465 thereby opens into the orifice formed by inner wall 446. Elbow 271 and connecting "T" 271' are both preferably injection molded from the same materials used for valve body 201.

The parts of inner surface 459 are designed to surround and sealably connect to a trimmed proximal end 467 of extension tube 90. Referring again to FIG. 2, membrane 158 comprises a surface 466 common to smaller lumen 156 and another surface 468 common to larger lumen 154.

As seen in FIG. 9, a top access to smaller lumen 156 is provided by removing a portion of the proximal end 467 of extension tube 90 to reveal a segment 470 of surface 466 and a lateral axial entry therefrom to lumen 156. The length of revealed segment 470 extends from the proximal end of extension tube 90 to the distal edge of male "T" connection 465 thereby providing a passageway from elbow 271 into connecting "T" 271' and therefrom into lumen 156 of extension tube 90 when extension tube 90 is fully inserted.

Surface 460 in combination with inferior proximal surface 462 is sized to compressively accept revealed surface 466 and the proximal portion of extension tube 90 under segment 470. In assembly, extension tube 90 is permanently and sealably affixed thereat by materials and methods which are known and available in the art. In similar fashion distal surface part 464 is sized to compressively fit around the circumference of extension tube 90 and is likewise sealably joined at the distal end of connecting "T" 271'.

Located distally from boss 240, body member 201 comprises an integral upwardly directed add-site 480. Add site 480 comprises an annular wall 482 comprising an exterior surface 484 and an interior surface 486 and a blunt upper edge 487. Interior surface 486 comprises an inferior aperture 488 which communicates with passageway 207 and a superior aperture 490. Thereby, vertical access is provided into passageway 207.

To provide an anaerobic seal for add-site 480, a membrane 492 is disposed as a cover for superior aperture 490. Membrane 492 comprises a top plate 494 comprising a top horizontal circular surface 496 and a bottom horizontal substantially circular surface 498. The exterior circumference of the top circular surface 496 joins a vertically disposed flange 500. Flange 500 comprises an external wall surface 502' and an inner wall surface 502. Inner wall surface 502 is sized to compressively merge with exterior surface 484.

Disposed medially from flange 500 and extending downward from bottom surface 498 is a second flange 504 which comprises an exterior surface 506. Second flange 504 is medially disposed from flange 500 a distance which is less than the width of annular wall 482, but a distance which permits flanges 500 and 504 of membrane 492 to compressively conform about the upper edge 487 of annular wall 482. Thus disposed, membrane 492 is bonded to the blunt upper edge 487 and contacting wall surfaces 484 and 486 to form the anaerobic seal. Membrane 492 may be molded from the same material as membrane 136 and is functionally similar, providing an anaerobic pathway for injecting biologically active liquids into passageway 207.

In use, valve fitting 200 is joined to tube 40 which provides a liquid pathway from a pressurized source 30, as seen in FIG. 1. Valve fitting is purged of any air and thereafter connected to a patient catheter 100 in a manner similar to that seen in FIG. 1. In an unattended state, pressurized liquid flows from source 30 to the patient catheter 100 through passageway 206.

Thereafter, at times determined by an attendant, a bolus of biologically active liquid is injected into add-site 480 in a manner similar to that seen in FIG. 7. By depressing actuator 284, flow is diverted from passageway 206 to passageway 207 to rapidly deliver the biologically active liquid to patient catheter 100 through the smaller cross section and volume of lumen 156, thereby clearing valve fitting 200 and extension tube 90 of the bolus of biologically active liquid without additional procedures or equipment and with a substantially dynamic dead space.

Thus, the operator maintains the flow of liquid through the smaller lumen 156, only so long as the procedure is efficacious for such delivery of biologically active liquid. After the biologically active bolus is delivered to patient catheter 100, the operator merely releases the actuator 282 and the memory of the material from which the disc-shaped top spring member 275 is made causes the valve member 270 to return to the unstressed, at rest position illustrated in FIGS. 10 and 11. When the catheter tube is removed from the patient, the extension set 10, if part of the device, is uncoupled from the source 30 and the tube 40, and patient catheter 100 and may be discarded.

In cases when it is important to deliver undiluted medicant to the distal end of a patient resident catheter, a multi-lumen catheter 100' as seen in FIG. 13 is used. Multi-lumen catheter 100' is seen to comprise a first larger lumen 154' and a relatively smaller lumen 156' having substantially the same relative sizes as lumens 154 and 156 of dual lumen tube 90.

Tube 90 is interconnected to catheter 100' through a connector 520. Connector comprises a first hollow connecting tube 522, a second hollow connecting tube 524, and a tube connecting body 526.

Body 526 comprises a first hollow end 528 and a second hollow end 530. Disposed between the first hollow end 528 and second hollow end 530 is a medial support section 532. Medial support section comprises a pair of orifices 534 and 536 interposed between the first hollow end 528 and second hollow end 530. Orifice 534 comprises a diameter which is substantially the same diameter as lumen 156 and a position which has the same radial relationship with orifice first hollow end 528 as lumen 156 has with the outside diameter of dual lumen tube 90. Therein tube 522 is solidly medially affixed.

Orifice 536 comprises a diameter and shape compatible with that of lumen 154. Orifice 536 is disposed relative to orifice 534 in the same relation that lumen 154 is disposed to lumen 156. Tube 524 having substantially the same outside shape and size as orifice 536 is solidly medially affixed therein.

To interconnect the flow paths of lumens 154 and 156 to connector 520, the distal end of tube 90 with lumen 156 aligned with tube 522 and lumen 154 aligned with tube 524 is inserted into the first hollow end 528 and releasibly, but firmly joined thereat. Similarly, to connect the flow paths of lumens 154' and 156' to connector 520, the proximal end of catheter 100' with lumen 156' aligned with tube 522 and lumen 154' aligned with tube 524 is inserted into the second hollow end and releasibly but firmly affixed thereat. So joined, the flow path of lumen 156 communicates solely and directly with the flow path of lumen 156', thereby providing a direct and undiluting pathway from extension set 10 to the distal end of patient resident catheter 100'.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. An apparatus for infusion of two medical liquids into a medical patient comprising:
   proximal lumen-defining means to receive a first medical liquid from a source;
   distal lumen-defining means by which the mentioned liquids are infused into the patient;
   intermediate lumen-defining means interposed for selective liquid communication to distal lumen-defining means;
   the intermediate lumen-defining means comprising a primary flow first lumen and a supplemental flow second lumen, the first and second lumens being disposed in parallel relationship;
   valve means by which normal flow of the first medical liquid passes from the proximal lumen through the first lumen and thence through the distal lumen to the patient can be selectively diverted into and through the second lumen and thence through the distal lumen to the patient;
   secondary source means associated with the second lumen to accommodate, without removal of liquid from the second lumen, selective introduction into the second lumen of a second medical liquid sandwiched as an isolated liquid segment between distal and proximal interfaces with the first medical liquid whereby the isolated liquid segment is pushed as a unit from the second lumen through the distal lumen into the patient without material commingling of the two liquids when the valve means cause said selective diversion of the flow of the first medical liquid into and through the second lumen.

2. An apparatus according to claim 1 wherein the intermediate lumen-defining means comprises wall means formed of synthetic resinous tubular material.

3. An apparatus according to claim 1 wherein the second lumen is substantially smaller than the first lumen.

4. An apparatus according to claim 1 wherein the intermediate lumen-defining means comprise synthetic resinous material having memory comprising collapsible wall means which accommodate selective lumen occlusion by external force imposed by the valve means so that, upon removal of the external valve means force, the memory of the material causes the lumen to be non-occluding.

5. An apparatus according to claim 4 wherein the valve means comprise pinch valve means by which the intermediate lumen-defining means are selectively collapsed to selectively occlude the first lumen and the second lumen respectively.

6. An apparatus according to claim 5 wherein the pinch valve means comprises at least one manually operable slider valve element.

7. An apparatus according to claim 1 wherein the secondary source means comprise a self-sealing diaphragm through which the second medical liquid is unitarily injected as a segregated liquid segment using a needle.

8. A method of infusing at least two medical liquids without substantial commingling into a medical patient at a single infusion site comprising the steps of:

displacing a first medical liquid from an effluent only source along a flow path-defining passageway between the source and the single patient infusion site;

providing a second normally non-flowing, normally static liquid containing by-pass passageway adjacent and in selective influent and effluent liquid communication with the flow path-defining passageway between the source and the infusion site;

introducing a second medical liquid into the static liquid contained within the by-pass passageway so that the second medical liquid comprises a bolus and is interposed between front and rear portions of but does not materially mix with the first medical liquid;

applying upstream pressure via the first medical liquid against a proximal portion of the second medical liquid bolus to push the second medical liquid bolus from the by-pass passageway into the flow path, along the flow path and into the patient through the infusion site.

9. A method of infusion into a patient a second medical liquid using a first medical liquid to displace the second medical liquid without substantially mixing of the two medical liquids comprising the steps of:

infusing the first medical liquid into the patient through a normally-flowing infusion lumen;

placing a quantity of the second medical liquid in series between fore and aft volumes of the first medical liquid in an infusion by-pass lumen without substantial mixing of the liquids;

diverting flow of the first medical liquid from the normally-flowing infusion lumen into the by-pass lumen upstream of the second medical liquid thereby causing the second medical liquid to be pushed from the by-pass lumen into and through a portion of the normally-flowing infusion lumen and thence into the patient without substantial mixing between the second medical liquid and the first medical liquid.

10. A method according to claim 9 wherein the first medical liquid is displaced by gravity from an effluent only source and thence through the normally-flowing infusion lumen including a distal catheter tube into the cardiovascular system of the patient.

11. A method according to claim 9 wherein the placing step comprises introducing the second medical liquid into the by-pass lumen through a self-sealing diaphragm without causing substantial mixing of the liquids.

12. A method according to claim 10 wherein the diverting step comprises causing the entire flow of the first medical liquid to be diverted from the normally-flowing lumen through the by-pass lumen accompanied by a cessation of flow in the normally-flowing lumen.

13. A method according to claim 12 wherein the causing and cessation steps occur responsive to valve actuation.

14. A method according to claim 13 wherein the valve actuation step occurs at a single site and comprises essentially simultaneously occluding the normally-flowing lumen and unoccluding the by-pass lumen.

15. A method according to claim 13 wherein the valve actuation comprises occluding the normally-flowing lumen and unoccluding the by-pass lumen responsive to pinch valve action.

16. A method of administering medical liquid to a patient comprising the steps of:

delivering a first medical liquid from a source through a hollow first infusion passage to the patient;

delivering a second medical liquid unitarily and substantially from a second source instantaneously to a hollow second infusion passage;

holding the second medical liquid as an isolated liquid segment without a significant commingling with any other liquid in the second infusion passage under non-flow conditions;

thereafter diverting flow of the first medical liquid from the first infusion passage into the hollow second infusion passage behind the isolated segment of the second medical liquid to push the isolated segment of the second medical liquid therefrom substantial as a segregated liquid into the patient.

* * * * *